United States Patent [19]

Donenfeld

[11] Patent Number: 4,685,457

[45] Date of Patent: Aug. 11, 1987

[54] ENDOTRACHEAL TUBE AND METHOD OF INTUBATION

[76] Inventor: Roger F. Donenfeld, 201 E. 19th St., Apt. 4L, New York, N.Y. 10003

[21] Appl. No.: 902,302

[22] Filed: Aug. 29, 1986

[51] Int. Cl.⁴ .............................................. A61M 16/00
[52] U.S. Cl. .......................... 128/207.14; 128/207.15; 604/95
[58] Field of Search ...................... 128/207.14, 207.15, 128/3, 4, 8, 10, 17, 20; 604/93, 95

[56] References Cited

U.S. PATENT DOCUMENTS

| | | |
|---|---|---|
| 1,863,234 | 6/1932 | Bacon . |
| 2,268,321 | 12/1941 | Flynn . |
| 2,498,692 | 2/1950 | Mains . |
| 3,416,531 | 12/1968 | Edwards . |
| 3,470,876 | 10/1969 | Barchilon . |
| 3,503,385 | 3/1970 | Stevens . |
| 3,552,384 | 1/1971 | Pierle . |
| 3,572,325 | 3/1971 | Bazell et al. . |
| 3,605,725 | 9/1971 | Bentov . |
| 3,605,750 | 9/1971 | Sheridan et al. . |
| 3,610,231 | 10/1971 | Takahashi . |
| 3,669,098 | 6/1972 | Takahashi . |
| 3,677,262 | 7/1972 | Zukowski . |
| 3,754,554 | 8/1973 | Felbarg . |
| 3,776,222 | 12/1973 | Smiddy . |
| 3,802,440 | 4/1974 | Salem et al. . |
| 3,810,474 | 5/1974 | Cross . |
| 3,860,007 | 1/1975 | Binard et al. . |
| 3,964,488 | 6/1976 | Ring et al. . |
| 3,996,939 | 12/1976 | Sheridan et al. . |
| 4,033,331 | 7/1977 | Guss et al. . |
| 4,063,561 | 12/1977 | McKenna . |
| 4,244,362 | 1/1981 | Anderson . |
| 4,257,421 | 3/1981 | Beal . |
| 4,329,983 | 5/1982 | Fletcher . |
| 4,449,522 | 5/1984 | Baum . |
| 4,454,887 | 6/1984 | Kruger . |
| 4,529,400 | 7/1985 | Scholten . |
| 4,589,410 | 5/1986 | Miller ............................ 128/207.15 |

Primary Examiner—Henry J. Recla
Attorney, Agent, or Firm—Wood, Herron & Evans

[57] ABSTRACT

An endotracheal tube for respirating a patient and the method of incubation of the tube comprises an elongated air tube having an inner wall and an outer wall spaced from the inner wall between which four passageways are circumferentially spaced approximately 90° apart and extend from the distal end of the tube to its proximal end. A control line is received within each passageway which is fixed to each end of the air tube but movable within the passageways therebetween. The air tube is inserted through an upper airway passage to a point near the trachea, and then the proximal end of the air tube is deflected to produce an equal and opposite deflection of the distal end into alignment with the trachea. In an alternative embodiment, a stylet having essentially the same design as the endotracheal tube herein, but with smaller external dimensions, is adapted for insertion into a standard endotracheal tube to manipulate the distal end of such tubes to facilitate intubation.

6 Claims, 5 Drawing Figures

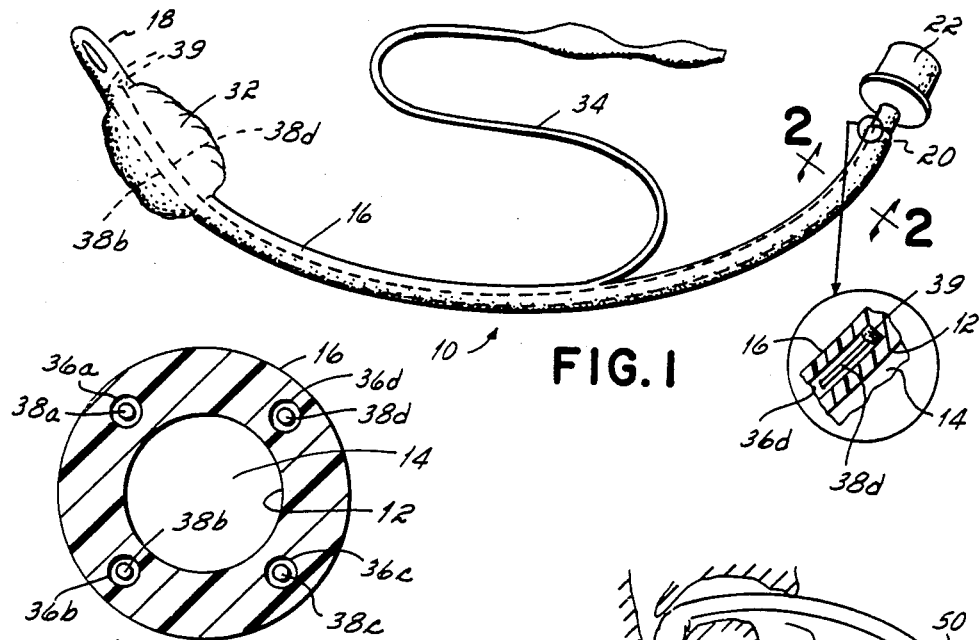
FIG.1
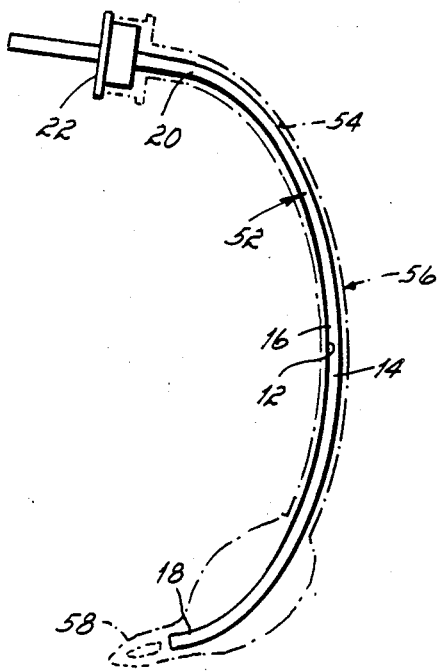
FIG.2
FIG.5
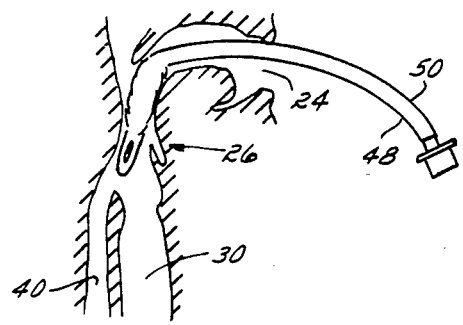
FIG.3
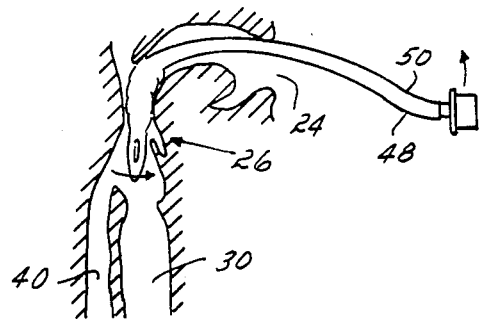
FIG.4

ENDOTRACHEAL TUBE AND METHOD OF INTUBATION

BACKGROUND OF THE INVENTION

This invention relates to endotracheal tubes, and, more particularly, to an endotracheal tube having a distal end which can be manipulated to facilitate intubation in the trachea of a patient.

Endotracheal tubes have been used for a number of decades to prevent upper airway obstruction or to facilitate artificial ventilation of unconscious or anesthetized patients. Standard endotracheal tubes comprise an elongated, flexible air tube which is curved or arcuate-shaped between its distal end and proximal end for insertion through the upper airway passages into the trachea. An inflatable bag-like structure or cuff is disposed about the exterior surface of the air tube at the distal end which is inflatable after the tube is in place to create an air-tight seal between the tube and tracheal wall. This prevents air being pumped by a respirator connected to the proximal end of the tube from escaping retrograde through the trachea and entering the oral and nasal passages.

The arcuate shape of prior art endotracheal tubes is intended to duplicate the path of the air one inhales so that when the distal end of the air tube is inserted through the oral or nasal passage it slides directly into the trachea instead of the esophagus. Conventional intubation techniques include inserting a laryngoscope into the mouth to anteriorly displace the tongue, lift the epiglottis and directly visualize the larnyx to intubate the trachea. Intubation of the trachea through the nasal air passages is more difficult because the pathway from the external nares into the trachea is circuitous and requires two bends of the endotracheal tube, virtually at right angles to one another. For some patients, intubation of the trachea either through the oral or nasal passages is routine.

In other patients, the intubation procedure can be difficult even for trained personnel. A difficult intubation may be anticipated in patients with short muscular necks, receeding jaws, large thick tongues, high arched palates, cervical spine or madibular immobility, hematoma, abcess or inflammation around the posterior pharynx or larynx, facial fractures or anatomical deviations from normal.

In order to perform the intubation procedure correctly, the distal end of the tube must be inserted within the trachea so that the lower cuff is positioned a few centimeters below the larynx to seal the trachea when inflated. Prior art endotracheal tubes are formed of a flexible plastic material to permit at least some deflection of the distal end of the tube during intubation by manipulating the remaining portion of the tube. However, once the distal end of the tube approaches the trachea and contacts the laryngeal region, it can become difficult to guide the distal end by manipulating the remaining portion of the tube. This is a particular problem for the conditions described above in which a difficult intubation can be anticipated. Because of the difficulty in controlling the movement of the distal end of prior art endotracheal tubes, intubation is often performed unsuccessfully either by failing to direct the tube a sufficient distance past the vocal chords or by moving the tube anteriorly into the esophagus.

The problems with the intubation procedure outlined above have been recognized in the prior art, and endotracheal tubes, catheters and stylets have been proposed which provide for controlled movement of the distal end during intubation. For example, U.S. Pat. Nos. 3,470,876; 3,605,725; and 2,498,692 all disclose catheters or tubes having an inner wall, an outer wall spaced from the inner wall and two or more spaced passageways formed between the inner and outer walls. Each of the passageways receives a line which is fixed at the distal end of the tube or catheter, and which is connected to a tensioning device mounted externally of the tube or catheter at its proximal end. Movement of the distal end of the tubes during intubation is achieved by selectively pulling or tensioning the lines with the tensioning devices, which, in turn, causes a deflection of the distal end fixedly connected to the lines.

The problems with the designs disclosed in the prior patents mentioned above are many. The tensioning devices for the lines, which are mounted exteriorly of the tubes in the patents mentioned above, are cumbersome, complicated and add substantially to the cost of the tubes, catheters or stylets which are disposable and not intended for reuse. In addition, at least a portion of each line at the proximal end of the tubes is exposed and could be broken or otherwise damaged prior to or during an intubation procedure. The endotracheal tubes and catheters in the prior art often require both hands to intubate the trachea which increases the difficulty of the procedure, particularly in certain patients as discussed above.

SUMMARY OF THE INVENTION

It is therefore an objective of this invention to provide a one-piece, self-contained endotracheal tube, and method of intubation, which permits controlled manipulation of the distal end of the endotracheal tube throughout the intubation procedure to ensure proper positioning of the tube within the trachea.

This objective is accomplished by an endotracheal tube which comprises an elongated flexible air tube having a proximal end adapted for connection externally of the patient to a respirator, and a distal end having a cuff fixed to its outer wall for insertion within the trachea. The air tube is curved between the distal and proximal ends to facilitate its insertion within the trachea, as described below. The air tube is formed with an a inner wall defining a primary lumen and an outer wall spaced from the inner wall. Circumferentially spaced passageways are formed between the inner and outer walls of the air tube which extend from its distal end to the proximal end.

In a presently preferred embodiment, a string or control line such as a monafilament, nylon line is carried within each of the passageways formed between the inner and outer walls of the air tube. The control lines are fixedly mounted by a weldment or other means to both the distal end and the proximal end of the air tube, but are movable within the passageways between such ends. Preferably, four passageways are provided which are spaced 90° apart so that the control lines are evenly spaced about the circumference of the air tube.

In an intubation procedure, the distal end of the air tube is first inserted through the oral or nasal passage of the patient to a point near the larynx. The attendant continues the intubation procedure by grasping the proximal end of the air tube, which is located exteriorly of the patient, and then bending the proximal end in the posterior direction to cause movement of the distal end an equal amount in the anterior direction so that the distal end aligns with the trachea.

Movement of the distal end of the air tube in response to manipulation of its proximal end is attributable to the orientation and attachment of the control lines within the passageways in the air tube. As mentioned above, each line is fixedly connected at the distal end and the proximal end of the air tube but movable within the passageways between such ends. When the proximal end of the air tube inserted within the patient is bent or deflected in one direction, e.g., in a posterior direction, the lines on the anterior side of the air tube undergo tension and are pulled in a proximal direction by the posterior movement of the proximal end. Since such lines are fixed at the distal end of the air tube, their proximal movement pulls on the distal end and bends it in an anterior direction for alignment with the trachea. In this manner, the movement of the distal end of the air tube can be carefully controlled to guide it through the larynx and into the trachea.

In another aspect of this invention, a stylet is provided for insertion into a standard endotracheal tube to guide it into the trachea in the same manner as described above. In a presently preferred embodiment, the stylet is a smaller version of the endotracheal tube herein which comprises a flexible tube having an inner wall, an outer wall spaced from the inner wall and four circumferentially spaced passageways formed between the inner and outer walls. A line is received within each passageway which is fixedly mounted to both the distal end and proximal end of the tube. Alternatively, the stylet can be a solid section of flexible plastic material formed with four spaced passageways, each of which receive a line.

The stylet of either embodiment is inserted within the primary lumen of a standard endotracheal tube and manipulated in the identical manner as the endotracheal tube of this invention described above, to guide the distal end of the standard endotracheal tube into the trachea.

Both the endotracheal tube and stylet of this invention are relatively simple and inexpensive in construction, and require no external devices or mechanisms for tensioning the control lines which control the motion of the distal end of the tube. The endotracheal tube and stylet herein are self-contained, the lines are not exposed and movement of the distal end is achieved by simple manipulation of the proximal end of the tube. The ease of manipulation of the endotracheal tube herein enables personnel without special skill or training to perform even relatively difficult intubations successfully,

DESCRIPTION OF THE DRAWINGS

The structure, operation and advantages of a presently preferred embodiment of this invention will become further apparent upon consideration of the following description, taken in conjunction with the accompanying drawings, wherein:

FIG. 1 is an isometric view of the endotracheal tube of this invention;

FIG. 2 is a cross sectional view of the endotracheal tube herein taken generally along line 2—2 of FIG. 1;

FIG. 3 is a view of the initial stages of insertion of the endotracheal tube herein through the oral passage of a patient toward the trachea;

FIG. 4 is a view illustrating the manipulation of the distal end of the endotracheal tube for alignment and insertion into the trachea; and FIG. 5 is an isometric view of the stylet of this invention shown in use with a standard endotracheal tube.

DETAILED DESCRIPTION OF THE INVENTION

Referring now to FIGS. 1 and 2, the endotracheal tube of this invention includes an elongated, flexible air tube 10 having an inner wall 12 defining a primary lumen 14 and an outer wall 16 spaced from the inner wall 12. The air tube 10 is formed of a flexible plastic material, and preferably a material having a slippery surface, i.e., a low coefficient of friction to aid in the intubation procedure. The air tube 10 is curved or arcuate in shape from its distal end 18 to its proximal end 20. The proximal end 20 is preferably provided with an adaptor 22 for connection externally of the patient to an artificial respirator (not shown). The curvature of the air tube 10 is intended to generally conform to the anatomical shape of the upper air passageways and throat of a patient, illustrated schematically in the drawings, including the oral passage 24, larynx 26 and trachea 30.

A bag-like membrane or cuff 32 is affixed to the exterior surface of the air tube 10 adjacent its distal end 18. The cuff 32 is connected to a source of air (not shown) by a tube 34 to permit inflation of the cuff 32 when the air tube 10 is in place within the trachea 30 as described below.

In a presently preferred embodiment, four passageways 36a-d are formed in the air tube 10 between its inner wall 12 and outer wall 16, and are circumferentially spaced along the air tube 10 at approximately 90° intervals. Each of the passageways 36a-d extend along the entire length of the air tube 10 from its distal end 18 to the proximal end 20. The passageways 36a-d each receive a filament or control line 38a-d, respectively, which are preferably formed of nylon or a monafilament line such as used in fishlines. The proximal end of each control line 38a-d is fixedly mounted to the proximal end 20 of the air tube 10 by a weldment 39, or other permanent means of attachment, and the distal end of each control line 38a-d is fixedly mounted to the distal end of the air tube 10 by a weldment 39. The major portion of the control lines 38a-d, between the proximal and distal ends 18, 20 of air tube 10, are free to move within the passageways 36a-d.

Referring now to FIGS. 3 and 4, an intubation procedure with the endotracheal tube of this invention is illustrated. Initially, the distal end 18 of the air tube 10 is inserted through the oral passage 24 of the patient and into the laryngeal region near the trachea 30 as shown in FIG. 3. At this location, the movement of the distal end 18 of air tube 10 must be controlled to ensure that the distal end 18 and cuff 32 move anteriorly into alignment with the trachea 30 and not posteriorly toward the esophagus 40.

Movement of the distal end 18 of air tube 10 is controlled by manipulation of the proximal end 20 of air tube 10. As the proximal end 20 is deflected in one direction toward the distal end 18, the distal end 18 is deflected an equal amount in the opposite direction toward the proximal end 20. This is because the control lines 38a-d are fixed at each end to the air tube 10.

For example, refer to FIG. 4. As mentioned above, control lines 38a-d are spaced within passageways 36a-d at about 90° intervals about the circumference of the air tube 10. When the proximal end 20 of air tube 10 is deflected in a generally posterior direction, i.e., toward the esophagus 40 as viewed in FIG. 4, the control lines on the anterior side 48 of the air tube 10, e.g., control lines 38c, d, are pulled posteriorly in the same direction in which the proximal end 20 is deflected. This is because such control lines 38c, d are fixedly mounted to the proximal end 20 of air tube 10 and are also movable within the passageways. In response to this posterior movement of the proximal end 20 of air tube 10 and the proximal end of the control lines 38c, d, the distal ends of such control lines 38c, d connected to the distal end 18 of air tube 10 are tensioned and pulled toward the proximal end 20. In turn, the distal end 18 of air tube 10 is deflected anteriorly with respect to the trachea 30 by such movement of the control lines 38c, d into alignment with the trachea 30. Movement of the proximal end 20 in one direction is therefore duplicated by an equal movement of the distal end 18 in the opposite direction.

Since four control lines 38a–d are employed, different control lines are tensioned with the movement of the proximal end 20 of air tube 10 in different directions. If the proximal end 20 of air tube 10 is deflected anteriorly relative to the trachea 30, for example, the control line 38a, b on the posterior side 50 of the air tube 10 are tensioned causing the distal end 18 of the air tube 10 to be deflected an equal amount in the opposite or posterior direction. The same applies where the proximal end 20 of the air tube 10 is deflected laterally in one direction; i.e., the distal end 18 is deflected an equal amount in the opposite, lateral direction. In this manner, movement of the distal end 18 of air tube 10 is carefully controlled to guide the distal end 18 directly into the trachea 30.

Referring now to FIGS. 4 and 5, a stylet 52 according to this invention is illustrated. The stylet 52 is similar to the endotracheal tube described above, and the same reference numbers are employed to indicate common elements of both structures. The stylet 52 differs from endotracheal tube in that it does not employ a cuff 32 or air supply tube 34, but is otherwise identical to air tube 10. The stylet 52 is adapted for insertion into the primary lumen 54 of a standard endotracheal tube 56. Movement of the stylet 52 is identical to that described above for the air tube 10, and such motion is imparted to the standard endotracheal tube 56 so that the distal end 58 of endotracheal tube 56 may be more easily inserted into the trachea 30.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof.

For example, it is contemplated that the number of passageways 36a–d formed between the inner wall 12 and outer wall 16 of air tube 10 could be reduced to two or three passageways and provide sufficient manipulation of the distal end 18 for at least simple intubation procedures. In addition, the stylet 52 may be formed of a solid section of flexible plastic, eliminating its primary lumen, with the passageways which receive the control lines extending through the solid section.

Therefore, it is intended that the invention not be limited to the particular embodiment disclosed as the best mode contemplated for carrying out this invention, but that the invention will include all embodiments falling within the scope of the appended claims.

What is claimed is:

1. An endotracheal tube for respirating a patient comprising:
    an elongated, flexible air tube having a deflectable proximal end adapted to be located external to the patient and a deflectable distal end adapted to be located within the trachea of the patient, said air tube being formed with an inner wall and an outer wall spaced from said inner wall;
    a plurality of circumferentially spaced passageways formed in said air tube between said inner wall and said outer wall, said passageways extending substantially parallel to one another and longitudinally between said distal end and said proximal end of said air tube;
    a control line disposed within each of said passageways, each of said control lines being fixedly mounted at one end to said distal end of said air tube and fixedly mounted at the other end to said proximal end of said air tube, said control lines being movable within said passageways between said distal and proximal ends of said air tube;
    said proximal end of said air tube being deflectable in a direction which selectively tensions at least one of said control lines to thereby deflect said distal end of said air tube.

2. The endotracheal tube of claim 1 in which said air tube is formed with four passageways spaced 90° apart.

3. The endotracheal tube of claim 1 in which each of said control lines is mounted by a weldment to said distal end and to said proximal end of said air tube.

4. A stylet for manipulating an endotracheal tube having a primary lumen and distal and proximal ends, comprising:
    an elongated tube having a deflectable proximal end and a deflectable distal end, said tube being formed with a plurality of circumferentially spaced passageways extending substantially parallel to one another and longitudinally between said distal end and said proximal end;
    a control line disposed within each of said passageways, each of said control lines being fixedly mounted at one end to said distal end of said tube and fixedly mounted at the other end to said proximal end of said tube, said control lines being movable within said passageways between said distal and proximal ends of said tube;
    said tube being insertable within said primary lumen of the endotracheal tube so that said distal end of said tube is positioned at the distal end of the endotracheal tube, said proximal end of said tube being deflectable in a direction which selectively tensions at least one of said control lines to thereby deflect said distal end of said tube.

5. The method of inserting an endotracheal tube into the trachea of a patient, comprising:
    inserting the distal end of an elongated flexible air tube through the oral or nasal passage of a patient to a position near the trachea, said air tube including an inner wall, an outer wall spaced from said inner wall and circumferentially spaced passageways formed between said inner wall and said outer wall and extending substantially parallel to one another and longitudinally from said distal end of said air tube to the proximal end of said air tube, said air tube having a control line within each said passageways having opposed ends fixedly mounted to said distal end and said proximal end of said air tube and movable in said passageways between said distal end and proximal end;

deflecting said proximal end of said air tube in a direction which selectively tensions at least one of said control lines to effect movement of said distal end of said air tube for guiding said distal end of said air tube into the trachea.

6. The method of manipulating the distal end of an endotracheal tube having a primary lumen for insertion into the trachea of a patient, comprising:

inserting a stylet within the primary lumen of the endotracheal tube, said stylet including a tube having a proximal end and a distal end, said distal end of said stylet being adjacent the distal end of said endotracheal tube when inserted, said tube being formed with circumferentially spaced passageways extending substantially parallel to one another and longitudinally between the distal and proximal ends of the tube, each of said passageways receiving a control line having opposed ends fixedly mounted to said distal end and proximal end of said tube and movable in said passageways between said distal and proximal ends;

deflecting said proximal end of said stylet tube in a direction which selectively tensions at least one of said control lines to effect movement of said distal end of said stylet tube, said distal end of said stylet tube engaging the distal end of the endotracheal tube for moving and guiding the distal end of the endotracheal tube into the trachea.

* * * * *